US010188470B2

(12) United States Patent
Bailey et al.

(10) Patent No.: US 10,188,470 B2
(45) Date of Patent: Jan. 29, 2019

(54) MINIMALLY INVASIVE SURGICAL INSTRUMENT TO PROVIDE NEEDLE-BASED THERAPY

(71) Applicant: INTUITIVE SURGICAL OPERATIONS, INC., Sunnyvale, CA (US)

(72) Inventors: David W. Bailey, Portola Valley, CA (US); Simon P. DiMaio, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/943,511

(22) Filed: Apr. 2, 2018

(65) Prior Publication Data

US 2018/0221095 A1  Aug. 9, 2018

Related U.S. Application Data

(63) Continuation of application No. 13/768,313, filed on Feb. 15, 2013, now Pat. No. 9,931,167.
(Continued)

(51) Int. Cl.
*A61B 34/30* (2016.01)
*A61B 90/11* (2016.01)
(Continued)

(52) U.S. Cl.
CPC .............. *A61B 34/30* (2016.02); *A61B 90/11* (2016.02); *A61B 18/1477* (2013.01);
(Continued)

(58) Field of Classification Search
CPC ..................... A61B 34/30; A61B 34/70–34/74
(Continued)

(56) References Cited

U.S. PATENT DOCUMENTS

| 5,737,500 A | 4/1998 | Seraji et al. |
| 5,820,623 A | 10/1998 | Ng |

(Continued)

FOREIGN PATENT DOCUMENTS

| CN | 102186396 A | 9/2011 |
| JP | 2010082189 A | 4/2010 |

(Continued)

OTHER PUBLICATIONS

Extended European Search Report for Application No. 13748878.9, dated Sep. 18, 2015, 5 pages.
(Continued)

*Primary Examiner* — Carl H Layno
*Assistant Examiner* — Dacheng Xie
(74) *Attorney, Agent, or Firm* — Haynes and Boone, LLP (57) ABSTRACT

A surgical instrument is provided that includes a first input mechanism having axial slots formed in a periphery and a second input mechanism having helical slots formed in a surface. The instrument also includes an insert having pins extending from a surface thereof, the insert coupled to the second input mechanism such that the one or more pins extend into the helical slots, and a surgical device coupled to an end. The surgical device is moved in a first degree of freedom in response to a mechanical driving force applied to both the first input mechanism and the second input mechanism, respectively, and the surgical device is moved in a second degree of freedom in response to a mechanical driving force applied to the second input mechanism while the first input mechanism is held stationary.

20 Claims, 6 Drawing Sheets

Related U.S. Application Data (60) Provisional application No. 61/599,300, filed on Feb. 15, 2012.

(51) Int. Cl.
*A61B 18/14* (2006.01)
*A61B 17/00* (2006.01)
*A61B 17/34* (2006.01)

(52) U.S. Cl.
CPC .............. *A61B 2017/00331* (2013.01); *A61B 2017/00477* (2013.01); *A61B 2017/3409* (2013.01)

(58) Field of Classification Search
USPC ...... 600/429, 564, 566–568; 606/1, 80, 130, 606/167, 170, 171, 185; 318/568.11; 74/20–24, 425.5, 840, 841
See application file for complete search history.

(56) References Cited

U.S. PATENT DOCUMENTS

| | | |
|---|---|---|
| 6,245,028 B1 | 6/2001 | Furst et al. |
| 6,331,181 B1 | 12/2001 | Tierney et al. |
| 6,665,554 B1 | 12/2003 | Charles et al. |
| 6,723,106 B1 | 4/2004 | Charles et al. |
| 7,155,316 B2 | 12/2006 | Sutherland et al. |
| 7,955,322 B2 | 6/2011 | Devengenzo et al. |
| 8,005,571 B2 | 8/2011 | Sutherland et al. |
| 2001/0013764 A1 | 8/2001 | Blumenkranz et al. |
| 2005/0234327 A1 | 10/2005 | Saracen et al. |
| 2006/0045672 A1 | 3/2006 | Maynard et al. |
| 2006/0161136 A1 | 7/2006 | Anderson et al. |
| 2008/0004632 A1 | 1/2008 | Sutherland et al. |
| 2008/0314181 A1 | 12/2008 | Schena |
| 2009/0024141 A1 | 1/2009 | Stahler et al. |
| 2009/0247859 A1 | 10/2009 | Daum et al. |
| 2009/0326365 A1 | 12/2009 | Goldenberg et al. |
| 2010/0041938 A1 | 2/2010 | Stoianovici et al. |
| 2010/0056900 A1 | 3/2010 | Whitcomb et al. |
| 2010/0069920 A1 | 3/2010 | Naylor et al. |
| 2010/0198052 A1 | 8/2010 | Jenkins et al. |
| 2011/0071380 A1 | 3/2011 | Goldenberg et al. |
| 2011/0201965 A1* | 8/2011 | Hibner .............. A61B 10/0275 600/567 |
| 2011/0238083 A1 | 9/2011 | Moll et al. |
| 2013/0209208 A1 | 8/2013 | Bailey et al. |
| 2013/0211401 A1 | 8/2013 | Bailey et al. |
| 2013/0211422 A1 | 8/2013 | Bailey |

FOREIGN PATENT DOCUMENTS

| | | |
|---|---|---|
| WO | WO-0126865 A1 | 4/2001 |
| WO | WO-0200130 A1 | 1/2002 |
| WO | WO-2004105578 A2 | 12/2004 |
| WO | WO-2007041094 A1 | 4/2007 |

OTHER PUBLICATIONS

International Search Report and Written Opinion for Application No. PCT/US2013/026406, dated Jun. 13, 2013, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

MINIMALLY INVASIVE SURGICAL INSTRUMENT TO PROVIDE NEEDLE-BASED THERAPY

RELATED APPLICATIONS

This application is a continuation of U.S. patent application Ser. No. 13/768,313, filed on Feb. 15, 2013, which on Mar. 14, 2018 issued as U.S. Pat. No. 9,931,167, and claims priority to U.S. Provisional Patent Application Ser. No. 61/599,300, filed on Feb. 15, 2012, each of which is herein incorporated by reference in its entirety.

BACKGROUND

1. Technical Field

The present disclosure is related to a minimally invasive surgical instrument. In particular, the present disclosure is related to a minimally invasive surgical instrument for providing needle-based therapy including ablation therapy.

2. Discussion of Related Art

Minimally invasive surgery is known under various names (e.g., endoscopy, laparoscopy, arthroscopy, endovascular, keyhole, etc.), often specific to the anatomical area in which work is done. Such surgery includes the use of both hand-held and teleoperated/telemanipulated/telepresence (robot assisted/telerobotics) equipment, such as the da Vinci® Surgical System commercialized by Intuitive Surgical, Inc. of Sunnyvale, Calif. Both diagnostic (e.g., biopsy) and therapeutic procedures may be performed using such robot assisted equipment. Instruments may be inserted into a patient percutaneously via surgical incision or via natural orifice. Although teleoperative surgery using the da Vinci® Surgical System provides great benefits over, for instance, many hand-held procedures, for some patients and for some anatomical areas the da Vinci® Surgical System is unable to effectively access a surgical site. For example, the da Vinci® Surgical System may be inadequate for performing certain types of surgeries and therapies, including needle-based surgeries and percutaneous procedures such as prostate focal therapy.

Prostate cancer is among the most common noncutaneous cancers in American men. There are two common screening methods for prostate cancer, namely the prostate-specific antigen test (PSA) and the digital rectal exam (DRE). The PSA test, which determines a likelihood of prostate cancer from antigen concentrations in the blood sample, is not conclusive. In the DRE, the physician can determine whether the prostate gland is enlarged or there are abnormal nodules present. In either case, needle biopsies are often recommended to determine if tumors exist and whether or not any tumor is benign or malignant. Each year 1.5 million core needle biopsies are performed, yielding several hundred thousand new cases of prostate cancer. In many cases, early detection of the cancer results in higher efficacy of the treatment methods utilized. Further, MRI-guided needle based therapies (biopsies, localized laser ablations, delivery of implantable seeds utilized in low-dose-rate (LDR) permanent brachytherapy, which is a common treatment for prostrate cancer, or other treatment) have been demonstrated to be successful. However, manipulation of the needle in the confined space afforded by the typical MRI instrument has proven challenging.

What is needed is a minimally invasive surgical instrument that can be used to perform image guided needle-based therapies and surgeries.

SUMMARY

Consistent with some embodiments, a minimally invasive surgical instrument is provided. The surgical instrument includes a first input mechanism having one or more axial slots formed in a periphery therein, the input mechanism coupled to a first mechanical driving mechanism, and a second input mechanism having one or more helical slots formed in a surface therein, the second input mechanism coupled to a second mechanical driving mechanism. The instrument also includes an insert having one or more pins extending from a surface thereof, the insert coupled to the first input mechanism and the second input mechanism such that the one or more pins extend out of the axial slots into the helical slots, and a surgical device coupled to an end of the insert. Consistent with some embodiments the surgical device is moved in a first degree of freedom in response to a mechanical driving force applied to both the first input mechanism and the second input mechanism by the first and second driving mechanisms, respectively, and the surgical device is moved in a second degree of freedom in response to a mechanical driving force applied to the second input mechanism by the second driving mechanism while the first input mechanism is held stationary.

Consistent with some embodiments, there is further provided a minimally invasive surgical instrument including a surgical device coupled to an end of a tubular insert, the insert having one or more pins extending from a surface of the tubular insert and a first tubular input mechanism, the tubular insert arranged to be concentrically within the first tubular input mechanism, wherein the first tubular input mechanism includes slots formed along an axis of the first tubular input mechanism and a hole at a first end of the first tubular input mechanism, wherein the one or more pins of the tubular insert extend through the slots and the surgical device extends through the hole. The instrument also includes a second tubular input mechanism concentrically surrounding the first tubular input mechanism and the tubular insert, the second tubular input mechanism including helical slots formed in an interior wall of the second tubular input mechanism, the one or more pins arranged to be received in the helical slots, wherein the surgical device is moved in a first degree of freedom in response to driving the first tubular input mechanism and the second tubular input mechanism, and the surgical device is moved in a second degree of freedom in response to driving the second tubular input mechanism while the first tubular input mechanism is held stationary.

Consistent with further embodiments, there is provided a minimally invasive surgical instrument that includes a first input mechanism having one or more axial slots formed in a periphery therein, the input mechanism coupled to a first mechanical driving mechanism and a second input mechanism having one or more helical slots formed in a surface therein, the second input mechanism coupled to a second mechanical driving mechanism. The instrument also includes an insert having one or more pins extending from a surface thereof, the insert coupled to the second input mechanism such that the one or more pins extend into the helical slots and a needle coupled to an end of the insert, wherein the needle is moved in a first degree of freedom in response to a mechanical driving force applied to both the first input mechanism and the second input mechanism by the first and second driving mechanisms, respectively, and the needle is moved in a second degree of freedom in response to a mechanical driving force applied to the second input mechanism by the second driving mechanism while the first input mechanism is held stationary.

Consistent with some embodiments, there is further provided a minimally invasive surgical instrument. The instrument includes a first input mechanism coupled to a first mechanical driving mechanism and coupled to a first hollow elastic tube that is bent at a first predetermined angle. The instrument also includes a second input mechanism configured to be coaxially arranged with the first input mechanism, the second input mechanism coupled to a second mechanical driving mechanism and coupled to a second hollow elastic tube that is bent in a second predetermined angle and surrounded by the first hollow elastic tube. The first and second hollow elastic tubes are configured to straighten when the first input mechanism and the second input mechanism are driven with respect to each other.

These and other embodiments will be described in further detail below with respect to the following figures.

BRIEF DESCRIPTION OF THE DRAWINGS

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Various mechanical, compositional, structural, electrical, and operational changes may be made without departing from the spirit and scope of this description and the claims. In some instances, well-known circuits, structures, and techniques have not been shown in detail in order not to obscure the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Figure 1:
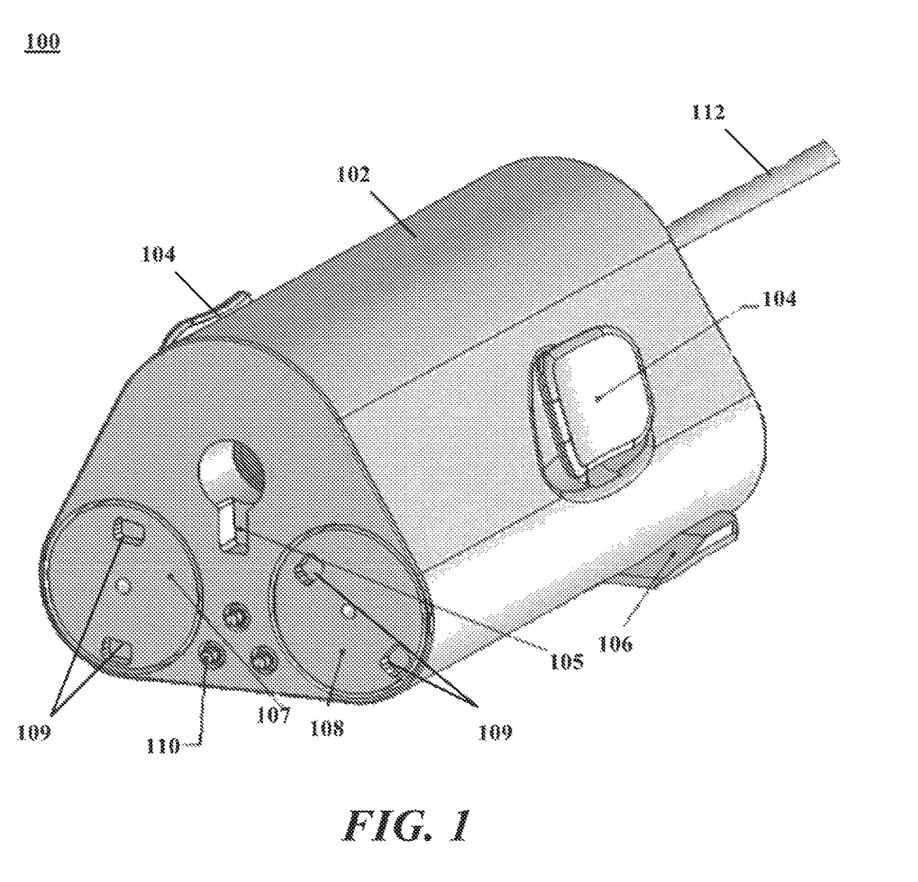
FIG. 1 is a diagram illustrating a minimally-invasive surgical instrument consistent with some embodiments.

FIG. 1 is a diagram illustrating a minimally-invasive surgical instrument consistent with some embodiments. As shown in FIG. 1, instrument 100 includes housing 102 and release levers 104. Instrument 100 further includes engagement features 105 and 106. Consistent with some embodiments, engagement features 105 and 106 may be provided to facilitate the engagement of instrument 100 to a mechanical manipulator (not shown). The mechanical manipulator may provide a mechanical driving force to instrument 100 through input discs 107 and 108. Input discs 107 and 108 include slots 109 for receiving tabs formed on driving discs of the mechanical manipulator (shown in FIG. 2A, below). Consistent with some embodiments, the mechanical manipulator may be a component of a robotic surgical system and may further move and position instrument 100 for performing surgical procedures. Such a robotic surgical system may correspond to a da Vinci® Surgical System, or a system such as described in the U.S. patent application entitled "Compact Needle Manipulator for Targeted Interventions," filed on Feb. 14, 2013, U.S. application Ser. No. 13/767,856, the entire contents of which are hereby incorporated by reference. Although embodiments disclosed herein are described primarily as being used in conjunction with a robotic surgical system, instrument 100 may be operated manually by an operator. Instrument 100 may be used along with an imaging device such as a computer tomography (CT) device, a magnetic resonance imaging (MRI) device, an ultrasound device, an X-ray device, or a positron emission tomography (PET) device. In such embodiments, the imaging device may be used to provide a real-time image of instrument 100 during surgery. Moreover, according to such embodiments, instrument 100 may be formed of materials that are radio-opaque or do not interfere with the magnetic fields produced by the imaging device to obtain the images. Examples of the materials that may be used to form instrument 100 are plastics, ceramics and non-ferrous metals.

Instrument 100 also includes an elongated hollow tube 112 attached at a distal end thereof. Consistent with some embodiments, elongated hollow tube 112 may be a needle and, throughout this disclosure, element 112 will be referred to as an elongated hollow tube and a needle interchangeably. Consistent with some embodiments, needle 112 may be used to puncture through cutaneous and subcutaneous tissue. Also consistent with some embodiments, a surgical device (not shown in FIG. 1) may be within needle 112 and may be advanced out of, and retracted into, needle 112. Surgical device 112 may be a catheter, an ablation device, a biopsy or tissue sampling device, an injector, or an optical biopsy probe, or a combination thereof. According to some embodiments, the surgical device is a catheter containing an ablation device. As explained in greater detail below, the surgical device may be movable in at least two degrees of freedom, including a degree of freedom that corresponds to movement along the axis of the surgical device, which may be coaxial with needle 112, and a degree of freedom that corresponds to rotation about the axis of the surgical device 112 (i.e., roll). According to some embodiments, needle 112 may also be moved in two degrees of freedom, including a degree of freedom that corresponds to rotation about the axis of needle 112 (i.e., roll), and a degree of freedom that corresponds to movement along the axis of needle 112. However, in accordance with some embodiments, movement of needle 112 in the degree of freedom along the axis of needle 112 may be facilitated by moving instrument 100 in that degree of freedom. The movement of instrument 100 may be performed by a not shown mechanical manipulator. Consistent with other embodiments, needle 112 and/or the surgical device may also be movable in other degrees of freedom.

Instrument 100 may also be usable with a fiducial arrangement that allows for tracking needle 112 by an imaging device, such as the CT and MRI devices described above. Such a fiducial arrangement may include a bead formed on a distal end of needle 112 that is implanted with a material that is visible when performing a CT or MRI image. According to other embodiments, needle 112 may be used as a delivery device that can be used to deliver implantable radiation sources utilized in brachytherapy. According to such embodiments, needle 112 may be replaced with a steerable stylet.

Returning to FIG. 1, instrument 100 also includes electrical connecting pins 110 at a proximal end thereof for coupling to an electrical interface on the mechanical manipulator of the robotic surgical system. Electrical connecting pins 110 may be coupled to an internal microprocessor and/or memory device by a circuit board within housing 102 (not shown). Consistent with some embodiments, a memory may include Dallas part No. DS 2505. The electrical pins 110 and the coupled internal microprocessor and/or memory device are further described in U.S. Pat. No. 6,331,181, assigned to Intuitive Surgical, Inc., and hereby incorporated by reference herein in its entirety. Electrical pins 110 may communicate information about instrument 100 to the mechanical manipulator such as an identification number of instrument 100, an identification of the type of surgical device, and a length of needle 112. Additional information that may be communicated to the mechanical manipulator through electrical pins 110 may include the type and range of motion that instrument 100 is capable of, or that instrument 100 is capable of imparting on needle 112 and the catheter and surgical device within or how to move the mechanical manipulator to obtain desired motions of needle 112 and the surgical device within. Information may also include a status of instrument 100, which may refer to the number of uses left of instrument 100 and/or needle 112, or an indication that instrument 100 and/or needle 112 is disposable, and has not been used, or has already been used and, thus, must be disposed.

Surgical instruments such as instrument 100 are typically sterile structures, often being sterilizable and/or being provided in hermetically sealed packages for use. However, the complex servo mechanism of instrument 100 and the mechanical manipulator may be difficult and/or impossible to fully sterilize between procedures. Consequently, a sterile drape will often cover at least a portion of the manipulator structures to maintain the sterile environment around the patient. As instrument 100 will be removed and replaced repeatedly during many procedures, the mechanical manipulator could potentially be exposed to contamination if the interface with instrument 100 is directly engaged. Consistent with some embodiments, needle 112 and/or instrument 100 may be a single use, disposable device. As such a single-use, disposable, sterile adaptor 200 (discussed in FIGS. 2A and 2B, below) may be provided to facilitate a sterile connection between instrument 100 and a mechanical manipulator. Sterile adaptor 200 may connect instrument 100 via engagement features 106 and electrical connecting pins 110.

Consistent with some embodiments, instrument 100 as described herein can be actively or passively positioned at a surgical site. Needle 112 and the surgical device within may be inserted with one or more segments of instrument 100 functioning in accordance with the description below. The instrument 100, surgical device 112, and the surgical device within may all be maneuvered using, e.g., image data from an imaging system at the guide probe's distal tip, real time image data from an external imaging system (e.g., ultrasound, fluoroscopy, MRI), preoperative image data and computer analysis of likely trajectory, and various combinations of these data.

Figure 2A:
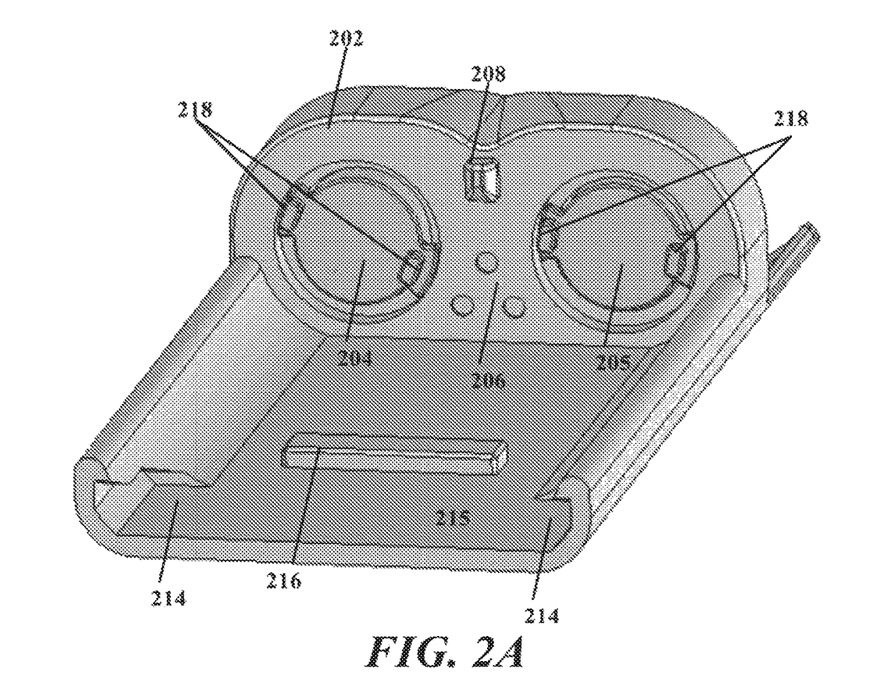
FIGS. 2A-2B are illustrations of a sterile adaptor, consistent with some embodiments.
Figure 2B:
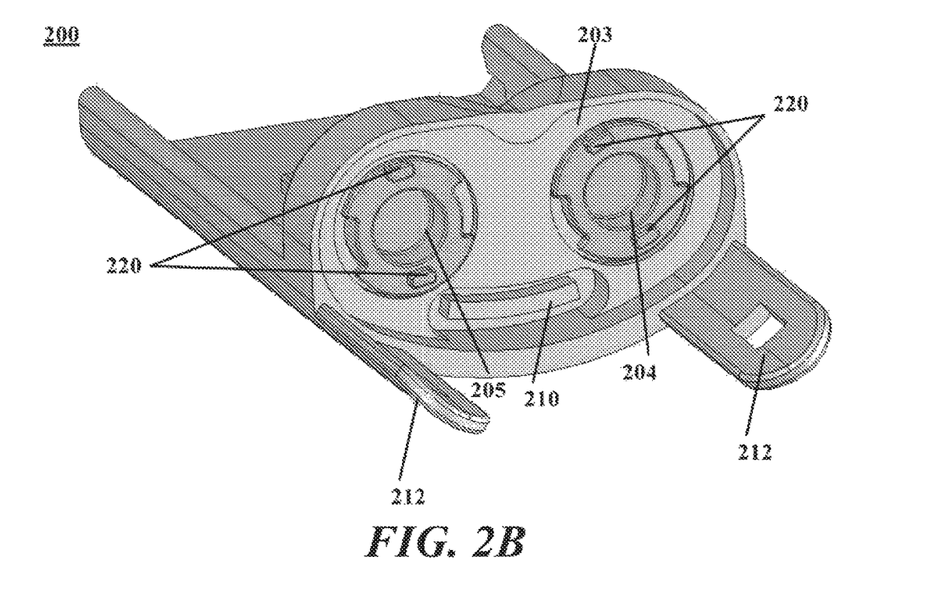

FIGS. 2A-2B are illustrations of a sterile adaptor, consistent with some embodiments. FIG. 2A illustrates a front view of sterile adaptor 200 and FIG. 2B illustrates a back view of sterile adaptor 200. The front view shown in FIG. 2A corresponds to a side that couples to instrument 100, and the back view shown in FIG. 2B corresponds to a side that couples to a mechanical manipulator. As shown in FIGS. 2A and 2B, sterile adaptor 200 includes a plate 202 on an instrument side and a manipulator engagement feature 203 on a manipulator side. Plate 202 has rotatable driving discs 204, electrical pin receivers 206, and a first instrument engagement feature 208 formed therein. On the back side, plate 202 also includes a line of four electrical contacts 210, three of the contacts transmitting information from pins 110 of instrument 100 to the coupled mechanical manipulator, and a loopback so that the manipulator can determine when adaptor 200 is coupled to the manipulator. Manipulator engagement features 203 and 212 are used to couple adaptor 200 to the mechanical manipulator. Sterile adaptor 200 further includes slots 214 formed on a support feature 215, and a spring bar 216 on support feature 215. As shown in FIG. 2A, rotatable driving discs 204 include tabs 218 for resilient engagement with slots 109 formed on input discs 107 and 108. As shown in FIG. 2B, rotatable driving discs 204 also include tabs 220 for resilient engagement with slots formed on a mechanical manipulator. Consistent with some embodiments, when instrument 100 is coupled to sterile adaptor 200, instrument 100 is positioned within sterile adaptor 200 such that electrical pins 110 are inserted into electrical pin receivers 206, first engagement feature 208 is inserted into engagement feature 105 while engagement feature 106 is inserted into slots 214, and tabs 218 are inserted into input disc slots 109. Applying force to release levers 104 will push spring bar 216 down allowing the disengagement of instrument 100 from sterile adaptor 200. When sterile adaptor 200 is coupled to a mechanical manipulator, engagement features 203 and 212 are resiliently engaged with mechanical manipulator and tabs 220 are engaged into slots formed on mechanical manipulator. Sterile adaptor 200 may be formed of materials that do not interfere with the magnetic fields produced by the imaging device to obtain the images. Examples of the materials that may be used to form sterile adaptor 200 are plastics, ceramics and non-ferrous metals. Sterile adaptor 200 may also be a disposable and/or single use device.

Figure 3A:
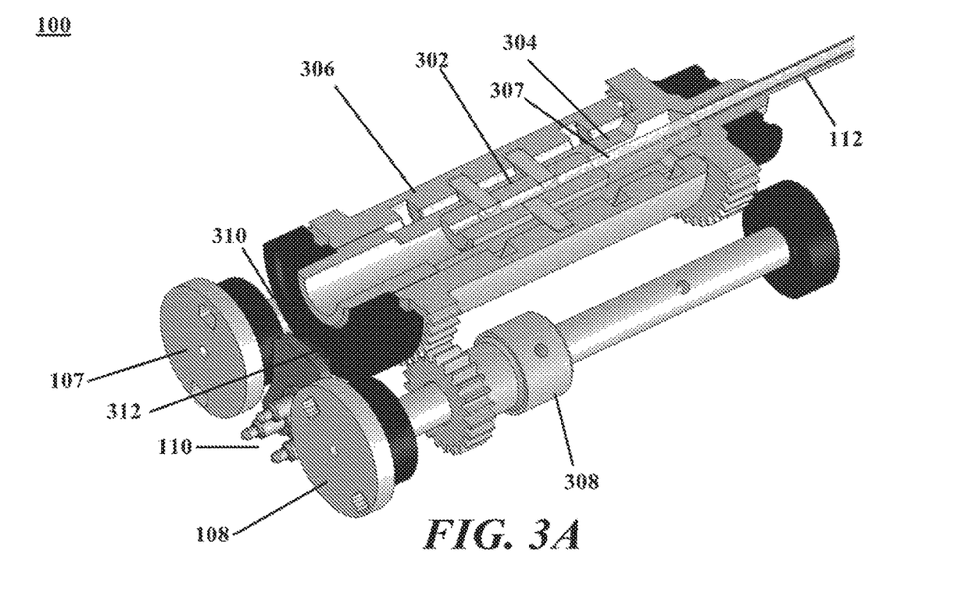
FIG. 3A is a diagram illustrating an internal view of a surgical instrument, consistent with some embodiments.

FIGS. 3A-3D are diagrams illustrating an internal view of surgical instrument 100, consistent with some embodiments. As shown in FIG. 3A, instrument 100 includes a shuttle insert 302 inside of a first input mechanism 304, both of which are inside of a second input mechanism 306. Needle 112 is coupled to first input mechanism 304 and extends out of the distal end of instrument 100, and a catheter 307 is coupled to shuttle insert 302 and extends out of the distal end of instrument 100 through first input mechanism 304, second input mechanism 306, and needle 112. Consistent with some embodiments, a surgical device such as an ablation device, may be within catheter 307, and may be extended out of needle 112 along with catheter 307. Similarly, catheter 307 and the surgical device may be retracted back within needle 112. Catheter 307 provides protection for the surgical device as it is inserted into, and maneuvered within, a body. Cooling fluid may also be in catheter 307 to cool the ablation or other surgical device. In one embodiment, instrument 100 comprises a 2.4 mm inch diameter needle 112 having a 1.6 mm inch diameter catheter 307 within that surrounds an ablation device for performing needle-based ablation therapy on a prostate. According to some embodiments, element 307 may be, instead of a catheter, a stylet of a core biopsy or tissue sampling instrument.

Input disc 108 is coupled to drive driving gear 308 and input disc 107 is coupled to drive driving gear 310. Driving gear 308 is coupled to second input mechanism 306 and, when input disc 108 coupled to driving gear 308 is driven, driving gear 308 rotates second input mechanism 306. Consistent with some embodiments, the rotation of second input mechanism 306 moves shuttle insert 302 and the coupled catheter 307 and surgical device within in a degree of freedom that corresponds to movement along the axis of catheter 307. Consequently, when driving gear 310 holds first input mechanism 304 stationary and driving gear 308 drives second input mechanism 306, catheter 307 and the enclosed surgical device may be moved in a degree of freedom about its axis thereby inserting catheter 307 and the surgical device into needle 112. Driving gear 310 is coupled to first input mechanism 304 and, when input disc 107 coupled to driving gear 310 is driven, driving gear 310 rotates first input mechanism 304. Consistent with some embodiments, first input mechanism 304 and second input mechanism 306 act as a differential such that the rotation of first input mechanism 304 assists in the movement of shuttle insert 302 and the coupled catheter 307 in a degree of freedom that corresponds to rotation about the axis of surgical device 112. Accordingly, shuttle insert 302 and the coupled catheter 307, as well as needle 112 coupled to first input mechanism 304, are moved in a degree of freedom that corresponds to rotation about the axis of catheter 307 when both driving gear 308 is driven to rotate second input mechanism 306 and driving gear 310 is driven to rotate first input mechanism 304. Further, shuttle insert 302 and the coupled catheter 307, and needle 112, are moved in a degree of freedom that corresponds to rotation about the axis of catheter 307 while shuttle insert 302 and coupled catheter 307 are also moved in a degree of freedom that corresponds to movement along the axis of catheter 307 when driving gear 308 holds second input mechanism 306 stationary and driving gear 310 is driven to rotate first input mechanism 304.

Returning to FIG. 3A, instrument 100 also includes a microprocessor 312 coupled to electrical pins 110 for communicating information about instrument 100 to a mechanical manipulator. Although not shown, instrument 100 may also include a memory device coupled to microprocessor 312 that stores information about instrument. Although instrument 100 shown in FIG. 3A shows a shuttle insert 302 within a first input mechanism 304 having axial slots 316, both of which are within a second input mechanism 306 having helical slots 326, the composition of instrument 100 is not so limited. For example, shuttle insert 302 could be within second input mechanism 306 with helical slots 326 both of which are within first input mechanism 304 having axial slots 316.

Figure 3B:
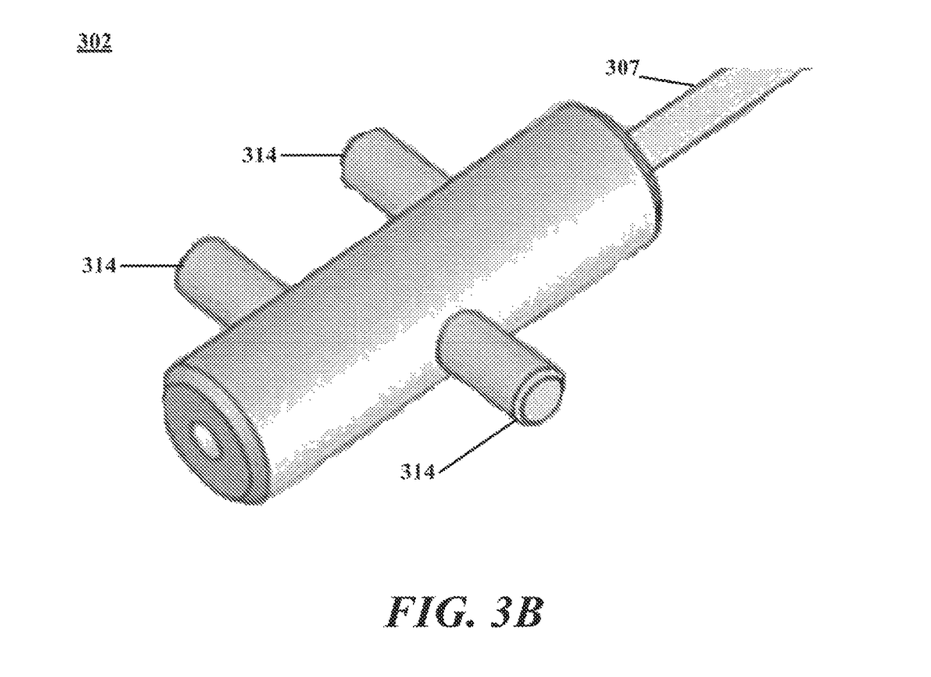
FIG. 3B is a diagram illustrating a shuttle insert of the surgical instrument, consistent with some embodiments.
Figure 3C:
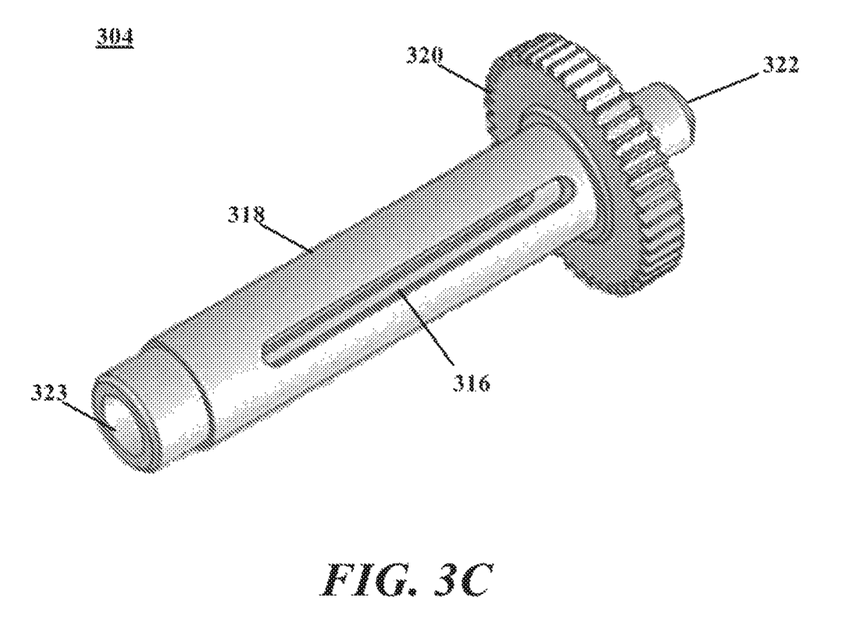
FIG. 3C is a diagram illustrating a first input mechanism of the surgical instrument, consistent with some embodiments.

FIG. 3B is a diagram illustrating shuttle insert 302, consistent with some embodiments. As shown in FIG. 3B, shuttle insert 302 includes a plurality of pins 314 attached to an exterior surface of shuttle insert 302 and catheter 307 coupled to a distal end of shuttle insert 302. FIG. 3C is a diagram illustrating first input mechanism 304, consistent with some embodiments. As shown in FIG. 3C, first input mechanism 304 includes one or more axial slots 316 formed along the periphery of a shaft 318 of first input mechanism 304 such that axial slots 316 extend along on axis of first input mechanism 304. Although not shown, in FIG. 3C, one or more identical axial slots 316 may be formed on the other side of first input mechanism 304. Consistent with some embodiments, pins 314 formed on shuttle insert may extend through axial slots 316. First input mechanism 304 also includes a circular toothed gear 320 formed at a distal end of first input mechanism 304. As shown in FIG. 3A, circular toothed gear 320 is coupled to driving gear 310 such that when driving gear 310 is driven, first input mechanism 304 is rotated. First input mechanism 304 also includes a distal hole 322 formed at the distal end of shaft 318 and a proximal hole 323 formed at a proximal end of shaft 318. Consistent with some embodiments, needle 112 is coupled to first input mechanism 304 at the distal end and distal hole 322 may include features for coupling, securing, and/or fastening needle 112 thereto. Moreover, catheter 307 coupled to shuttle insert 302 may extend out of proximal hole 323 and out of the proximal end of instrument 100 to the coupled mechanical manipulator.

Figure 3D:
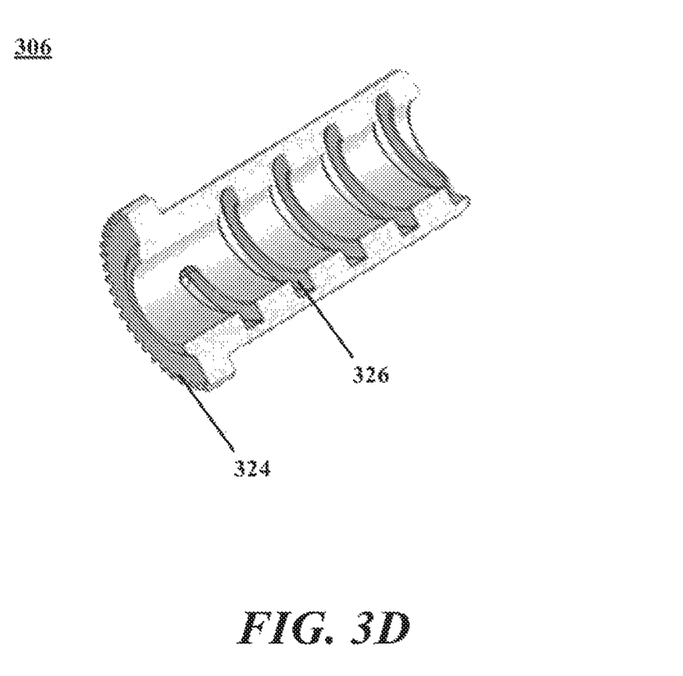
FIG. 3D is a diagram illustrating a second input mechanism of the surgical instrument, consistent with some embodiments.

FIG. 3D is a diagram illustrating a cross-section of second input mechanism 306, consistent with some embodiments. As shown in FIG. 3D, second input mechanism 306 includes a toothed gear 324, which, as shown in FIG. 3A, is coupled to driving gear 308. When driving gear 308 is driven, second input mechanism 306 is rotated. Second input mechanism 306 also includes a plurality of helical slots 326 formed along an interior surface of second input mechanism 306 in a helical or corkscrew shape. Consistent with some embodiments, pins 314 of shuttle insert 302 fit into helical slots 326 such that when second input mechanism 306 is driven by driving gear 308 and first input mechanism 304 is held stationary, second input mechanism 306 rotates while pins 314 of shuttle insert 302 are advanced along helical slots 326. As pins 314 are advanced along helical slots 326, shuttle insert 302 and coupled catheter 307 is moved in a first degree of freedom, along an axis of catheter 307, advancing or retracting shuttle insert 302 and coupled catheter 307.

Figure 4:
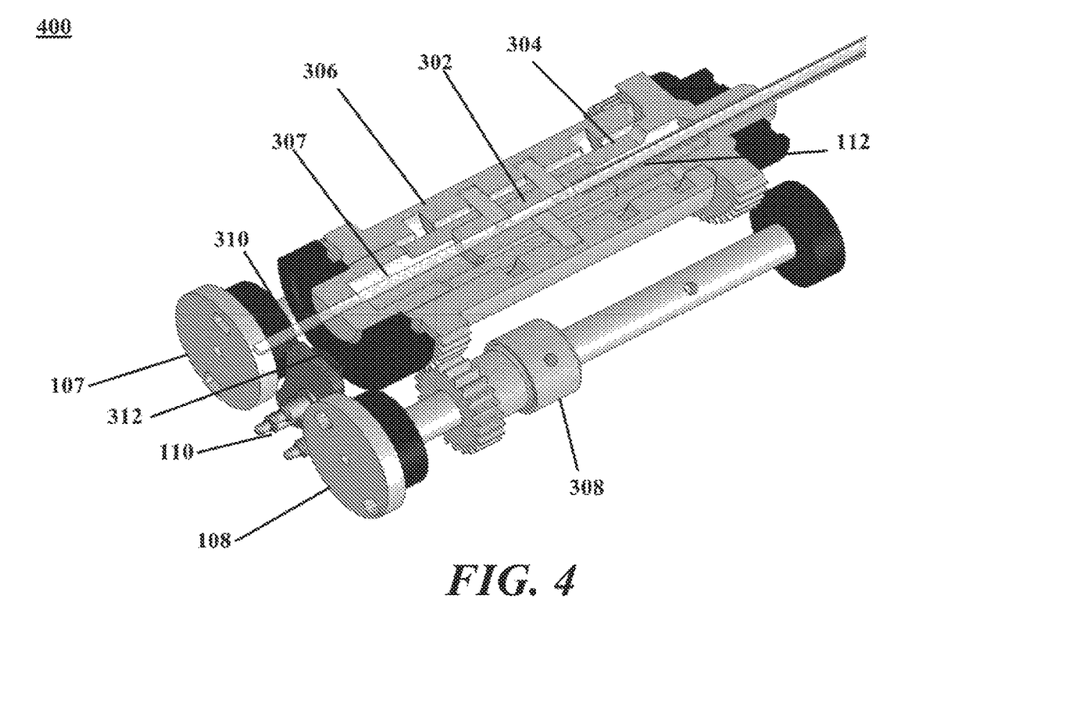
FIG. 4 is a diagram illustrating an internal view of another embodiment of a surgical instrument, consistent with some embodiments.

Consistent with some embodiments, a mechanical manipulator coupled to instrument 100 may move instrument 100 along an axis of catheter 307 in a direction opposite to the direction of an advancing shuttle insert 302 and coupled catheter 307 such that catheter 307 is advanced while instrument 100 and needle 112 are retracted. In such embodiments, needle 112 may be used to position catheter 307 and an enclosed surgical device such as an ablation device, at a location within a patient. Catheter 307 and the ablation device may then be advanced by driving second input mechanism 306 while holding first input mechanism 304 stationary. Instrument 100 is simultaneously moved opposite to the catheter and ablation device so that catheter and ablation device is exposed and able to perform ablation on a targeted region within the patient. Consistent with some embodiments, needle 112 may be attached to shuttle insert 302 instead of catheter 307 allowing for movement of needle 112 in a degree of freedom corresponding to axial movement along the axis of needle 112. Similarly, catheter 307 could be attached to first input mechanism 304 to provide rotational movement of catheter 307 while catheter 307 remains fixed axially. Alternatively, catheter 307 could be fixed directly to instrument housing FIG. 4 is a diagram illustrating an internal view of another embodiment of a surgical instrument. As shown in FIG. 4, instrument 400 is similar to instrument 100 shown in FIG. 3A, but needle 112 is coupled to shuttle insert 302, and catheter 307 is coupled to first input mechanism 304. When driving gear 310 holds first input mechanism 304 stationary and driving gear 308 drives second input mechanism 306, needle 112 may be moved in a degree of freedom along its axis thereby providing advancement and retraction movements of needle 112 into and out of instrument 400. This allows for needle 112 to be advanced to puncture cutaneous and subcutaneous tissue and then retracted leaving catheter 307 beneath the tissue after instrument 100 has been positioned by a human or robotic surgical device at a surgical location. Moreover, shuttle insert 302 and the coupled needle 112, as well as catheter 307 coupled to first input mechanism 304, are moved in a degree of freedom that corresponds to rotation about the axis of needle 112 when both driving gear 308 is driven to rotate second input mechanism 306 and driving gear 310 is driven to rotate first input mechanism 304. Further, shuttle insert 302 and needle 112, and catheter 307 are moved in a degree of freedom that corresponds to rotation about the axis of needle 112 while shuttle insert 302 and needle 112 are also moved in a degree of freedom that corresponds to movement along the axis of needle 112 when driving gear 308 holds second input mechanism 306 stationary and driving gear 310 is driven to rotate first input mechanism 304. Consequently, instrument 400 provides movement in two degrees of freedom, along the axis and rotation about the axis, for needle 112 coupled to shuttle insert 302, and provides movement in a single degree of freedom, rotation about the axis, for catheter 307 coupled to first input mechanism. Consistent with other embodiments, catheter 307 could be coupled directly to instrument housing 102 in embodiments where catheter 307 does not need to move in any degrees of freedom.

Figure 5A:
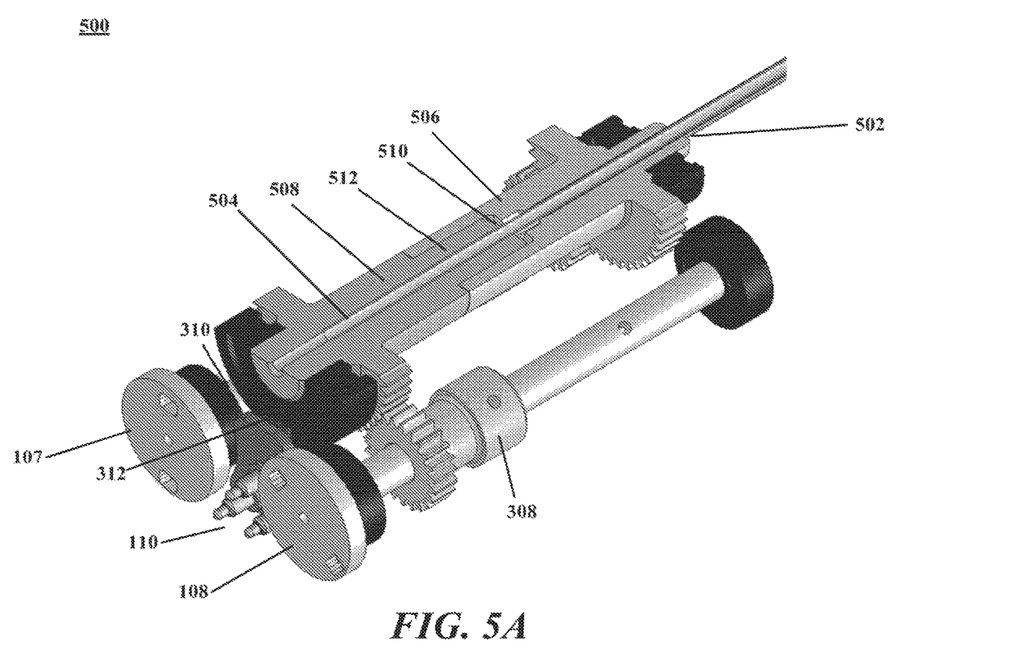
FIG. 5A is a diagram illustrating an internal view of a surgical instrument, consistent with some embodiments.

FIG. 5A is a diagram illustrating an internal view of a surgical instrument, consistent with some embodiments. Instrument 500 is similar to instrument 100 shown in FIG. 3A, and instrument 400 shown in FIG. 4, except that needle 112 and catheter 307 may each be replaced by a first hollow elastic tube 502 and a second hollow elastic tube 504. Consistent with some embodiments, hollow elastic tubes 502 and 504 could be made out of a super elastic material and may be bent with a fixed curve along a radial plane. For example, first hollow elastic tube 502 would be coupled to first input mechanism 506 and second hollow elastic tube 504 would be coupled to second input mechanism 508. Consistent with some embodiments, first input mechanism 506 may have a similar construction as first input mechanism 304, or a construction such as shown in FIG. 5A. Similarly, second input mechanism 508 may have a similar construction as first input mechanism 306, or a construction such as shown in FIG. 5A.

As shown in FIG. 5A, first input mechanism 506 and second input mechanism 508 are coaxially arranged. Input disc 108 is coupled to drive driving gear 308 and input disc 107 is coupled to drive driving gear 310. Driving gear 308 is coupled to second input mechanism 508 and, when input disc 108 coupled to driving gear 308 is driven, driving gear 308 rotates second input mechanism 508. Driving gear 310 is coupled to first input mechanism 506 and, when input disc 107 coupled to driving gear 310 is driven, driving gear 310 rotates first input mechanism 508. In this embodiment, shuttle 302 would not be necessary. When first hollow elastic tube 502 and second hollow elastic tube 504 are rotated with respect to one another by driving first input mechanism 506 and second input mechanism 508 as described above, the bent tubes could then be straightened due to the deformation caused to the tubes by the combination of bending and torsion applied by driving the first and second input mechanisms 506 and 508. Such embodiments could allow a surgeon to place a device, such as an ablation device or endoscope within the tubes, and have a 180° range of motion within a patient.

Figure 5B:
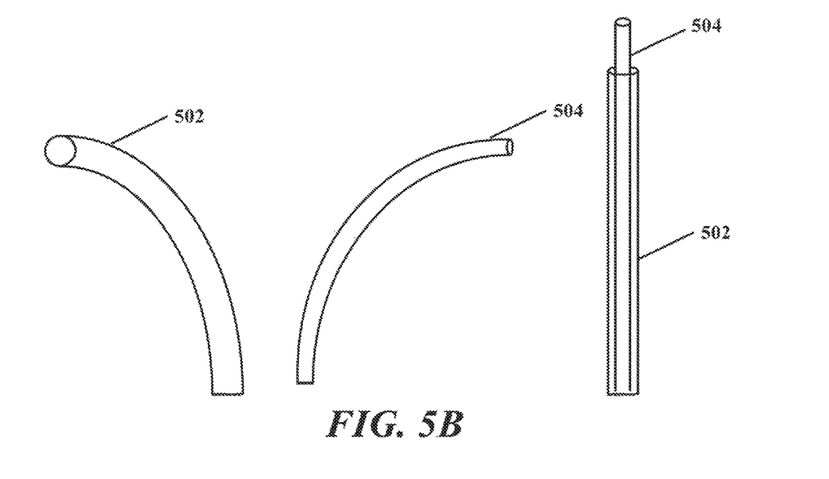
FIG. 5B is a diagram illustrating shapes of the first and second hollow elastic tubes and a shape of the combined tube, consistent with some embodiments.

FIG. 5B is a diagram illustrating shapes of the first and second hollow elastic tubes and a shape of the combined tube, consistent with some embodiments. As shown in FIG. 5B, first hollow elastic tube 502 may be bent at an angle to have a first shape, and second hollow elastic tube 504 may be bent at a different or same angle to have a second shape. When first hollow elastic tube 502 and second hollow elastic tube 504 are rotated with respect to one another by driving first input mechanism 506 and second input mechanism 508 as described above, the bent tubes could then be straightened due to the deformation caused to the tubes by the combination of bending and torsion applied by driving the first and second input mechanisms 506 and 508.

Embodiments as disclosed herein may provide a surgical instrument that can be used to perform needle-based and ablation therapies in patients. In particular, embodiments as disclosed herein may be used to perform image-guided focal therapies for prostate cancer. Moreover, embodiments as disclosed provide a surgical instrument that is capable of driving a surgical instrument in at least two degrees of freedom, wherein the driving force is provided by a robotic surgical system. The examples provided above are exemplary only and are not intended to be limiting. One skilled in the art may readily devise other systems consistent with the disclosed embodiments which are intended to be within the scope of this disclosure. As such, the application is limited only by the following claims.

What is claimed is:
1. A minimally invasive surgical instrument, comprising:
   a first input mechanism comprising a periphery and an axial slot in the periphery, wherein a first axial axis of rotation is defined for the first input mechanism;

a second input mechanism comprising a surface and a helical slot in the surface, wherein a second axial axis of rotation is defined for the second input mechanism, and wherein the second input mechanism surrounds the first input mechanism such that the second axial axis of rotation is coincident with the first axial axis of rotation;

an insert comprising a pin, wherein a third axial axis of rotation is defined for the insert, wherein the insert is surrounded by the first input mechanism such that the third axial axis of rotation is coincident with the first axial axis of rotation, and wherein the pin extends from the insert through the axial slot of the first input mechanism and into the helical slot of the second input mechanism; and a needle coupled to an end of the first input mechanism.

2. The instrument of claim 1, further comprising a surgical device extending axially through at least part of the needle.

3. The instrument of claim 2, wherein the surgical device comprises at least one of a catheter, an injector, a biopsy probe, an optical biopsy probe, an ablation device, or a tissue sampling device, or a combination thereof.

4. The instrument of claim 1, further comprising a surgical device extending axially through the insert and through at least part of the needle.

5. The instrument of claim 1, further comprising:
a first driving mechanism coupled to the first input mechanism such that the first driving mechanism rotates the first input mechanism about the first axial axis of rotation; and
a second driving mechanism coupled to the second input mechanism such that the second driving mechanism rotates the second input mechanism about the second axial axis of rotation;
wherein the first driving mechanism rotates the first input mechanism about the first axial axis of rotation independently of the second driving mechanism rotating the second input mechanism about the second axial axis of rotation; and
wherein the second driving mechanism rotates the second input mechanism about the second axial axis of rotation independently of the first driving mechanism rotating the first input mechanism about the first axial axis of rotation.

6. The instrument of claim 5, further comprising a catheter extending axially through at least part of the needle.

7. The instrument of claim 5, further comprising a catheter coupled to the insert and extending axially through the insert and through at least part of the needle.

8. The instrument of claim 5, further comprising a catheter coupled to the insert.

9. The instrument of claim 8, wherein on the condition that the first and second input mechanisms rotate together about their associated axial axes of rotation, the catheter rotates about but does not translate along the third axial axis of rotation.

10. The instrument of claim 8, wherein on the condition that the first input mechanism rotates around the first axial axis of rotation while the second input mechanism remains stationary, the catheter rotates about and translates along the third axial axis of rotation.

11. The instrument of claim 8, wherein on the condition that the first input mechanism remains stationary while the second input mechanism rotates about the second axial axis of rotation, the catheter translates along but does not rotate about the third axial axis of rotation.

12. The instrument of claim 8, wherein the catheter extends axially through at least part of the needle.

13. The instrument of claim 8, wherein the catheter extends axially through the insert and through at least part of the needle.

14. The instrument of claim 8, wherein:
the catheter comprises a surgical device; and
the surgical device comprises at least one of a mechanical biopsy probe, an optical biopsy probe, an ablation device, and a tissue sampling device, or a combination thereof.

15. The instrument of claim 1, further comprising:
a plurality of electric pins; and
a microprocessor coupled to the electrical pins, wherein the microprocessor is configured to transmit information about the instrument to an external manipulator via the electrical pins.

16. The instrument of claim 15, further comprising:
a catheter coupled to the first input mechanism, the catheter comprising a surgical device;
wherein the information comprises at least one of an identification number of the instrument, an identification of the surgical device, a length of the surgical device, or information describing how to move the first and second input mechanisms to obtain desired rotation and translation of the needle.

17. The instrument of claim 1, further comprising an arrangement of fiducial markers, the fiducial markers configured to be identified by at least one of computer tomography (CT) scanning, magnetic resonance imaging (MRI) scanning, X-ray imaging, ultrasound imaging, or positron emission topography (PET) imaging.

18. The instrument of claim 1, wherein the helical slot is formed on an interior surface of the second input mechanism, and the pin extends through an axial slot in the first input mechanism.

19. The instrument of claim 1, wherein:
the insert is arranged concentrically within the first input mechanism; and
the first input mechanism and the insert are arranged concentrically within the second input mechanism.

20. The instrument of claim 1, further comprising:
a housing enclosing the first input mechanism, the second input mechanism, and the insert;
wherein the housing comprises:
a hole at a first end, the hole arranged to be concentric with a surgical device coupled to the first input mechanism; and
a plurality of release levers arranged around a periphery of the housing.

* * * * *